US011497571B2

(12) United States Patent
Cau

(10) Patent No.: US 11,497,571 B2
(45) Date of Patent: Nov. 15, 2022

(54) SURGICAL ROBOTIC SYSTEM WITH CARRIAGE AND MANIPULATOR UNIT

(71) Applicant: MICROSURE B.V., Son (NL)

(72) Inventor: Raimondo Cau, Helmond (NL)

(73) Assignee: MICROSURE B.V., Son (NL)

( * ) Notice: Subject to any disclaimer, the term of this patent is extended or adjusted under 35 U.S.C. 154(b) by 701 days.

(21) Appl. No.: 16/488,778

(22) PCT Filed: Oct. 30, 2017

(86) PCT No.: PCT/EP2017/077791
§ 371 (c)(1),
(2) Date: Aug. 26, 2019

(87) PCT Pub. No.: WO2018/153512
PCT Pub. Date: Aug. 30, 2018

(65) Prior Publication Data
US 2020/0038126 A1 Feb. 6, 2020

(30) Foreign Application Priority Data
Feb. 27, 2017 (EP) .................... 17158110

(51) Int. Cl.
*A61B 34/37* (2016.01)
*A61B 46/10* (2016.01)
*A61B 34/00* (2016.01)
*B25J 3/00* (2006.01)
(52) U.S. Cl.
CPC .............. *A61B 34/37* (2016.02); *A61B 34/71* (2016.02); *A61B 46/10* (2016.02); *B25J 3/00* (2013.01)

(58) Field of Classification Search
CPC ......... A61B 34/37; A61B 34/71; A61B 46/10; A61B 34/30; A61B 34/70; A61B 2018/00178; B25J 3/00
See application file for complete search history.

(56) References Cited

U.S. PATENT DOCUMENTS 8,246,633 B2      8/2012  Omori
9,283,048 B2 *    3/2016  Kostrzewski .......... A61B 34/30
2006/0149418 A1   7/2006  Anvari

FOREIGN PATENT DOCUMENTS

WO    WO2013/018932 A1    2/2013

OTHER PUBLICATIONS

International Search Report and Written Opinion for PCT Patent App. No. PCT/EP2017/077791 (dated Mar. 7, 2018).

* cited by examiner

*Primary Examiner* — Julian W Woo
(74) *Attorney, Agent, or Firm* — McCoy Russell LLP

(57) ABSTRACT

Some embodiments are directed to a surgical robotic system including a suspension structure 1, a carriage 2 arranged to be mounted to the suspension structure, and a manipulator arm 3 arranged to be detachably docked to the carriage via a docking mechanism. The docking mechanism includes a first docking connector on the manipulator arm and a second docking connector on the carriage. The first and the second docking connector may establish an electrical connection between the manipulator arm and the carriage when the manipulator arm is docked. The manipulator arm includes a connector for connecting the manipulator arm via a cable to an electric power supply, and be configured to supply the carriage with the electrical power via the electrical connection when the manipulator arm is docked.

19 Claims, 8 Drawing Sheets

SURGICAL ROBOTIC SYSTEM WITH CARRIAGE AND MANIPULATOR UNIT

CROSS REFERENCE TO RELATED APPLICATIONS

This application is a national phase filing under 35 C.F.R. § 371 of and claims priority to PCT Patent Application No. PCT/EP2017/077791, filed on Oct. 30, 2018, which claims the priority benefit under 35 U.S.C. § 119 of European Patent Application No. 17158110.1, filed on Feb. 27, 2017, the contents of each of which are hereby incorporated in their entireties by reference.

BACKGROUND

Some embodiments of the presently disclosed subject matter relate to a surgical robotic system including a carriage and a manipulator unit, and a drape for use with the surgical robotic system.

Nowadays many surgeries are performed by surgical robots. These surgical robots may include so-called manipulator arms which generally have an end effector which handles a surgical tool acting upon the patient. It may be desirable for the manipulator arm to be movable along a suspension structure so as to allow the manipulator arm to be easily moved or repositioned during surgery.

For example, DE 10 2014 203 921 A1 describes a guide system for surgical robots. The guide system has a guide with at least one rail. At least one carriage is connected to and can be displaced along the guide. For that purpose, the carriage may include an electric motor. Furthermore, the carriage has a receptacle for at least one robot arm on which robot arm is detachably connectable with the receptacle.

Another example is US 20060149418 A1 which describes a robotic system for performing surgical operations using a plurality of robotic arms remotely controlled by at least one operator console. The system includes a track system configured for mounting to a patient support table and a plurality of base stations for operatively coupling each of the robotic arms to the track system, such that each of the base stations include a housing, a first connector for coupling the housing to the track system, the first connector configured for facilitating movement of the housing along the track system while coupled thereto, and a second connector for coupling the housing to the proximal end of at least one of the robotic arms, the second connector configured for providing at least one of power supply, control signaling, and data communication with respect to the coupled robotic arm.

Disadvantageously, the known robotic systems do not enable a user to attach and detach a manipulator arm during surgery in a sufficiently safe manner.

SUMMARY

An aspect of the presently disclosed subject matter is to obtain a surgical robotic system which allows a user to attach and detach a manipulator arm during surgery in a safer manner.

A first aspect of the presently disclosed subject matter provides a surgical robotic system, including a suspension structure including a rail, a manipulator unit including a carriage arranged to be mounted to the suspension structure, wherein the carriage includes an electric actuator for movement of the carriage along the rail, a manipulator arm arranged to be detachably docked to the carriage via a docking mechanism, the docking mechanism including a first docking connector on the manipulator arm and a second docking connector on the carriage, wherein the first and the second docking connector establish an electrical connection between the manipulator arm and the carriage when the manipulator arm is docked, wherein the manipulator arm includes a connector for connecting the manipulator arm via a cable to an electric power supply, and wherein the manipulator arm is configured to supply the carriage with the electrical power via the electrical connection when the manipulator arm is docked.

The above described surgical robotic system includes a carriage which is mounted to a suspension structure. As such, the carriage may be semi-permanently attached to the suspension structure and may not be intended to be removed during surgery. The carriage may be actuated by an electric actuator and thereby moved along a rail of the suspension structure. A manipulator arm is provided which may be docked to the carriage via a docking mechanism, which also allows undocking from the carriage. This enables the manipulator arm to be introduced and/or removed during surgery. For example, the manipulator arm may be attached when needed during the surgery, while at other times keeping the surgical space free by being detached from the carriage. Conversely, the manipulator arm may be removed from the carriage and thus from the surgical space when it is not needed anymore, when the surgeon needs better access to the surgery site, when a different manipulator arm is to be used, etc.

In order to operate the carriage, and in particular to actuate its electric actuator, the carriage may need to be connected to an electrical power supply. In the above described surgical robotic system, electrical power is provided to the carriage as follows. The manipulator arm includes a connector to which a cable may be connected by which, when connected, electrical power from an electrical power supply may be supplied to the manipulator arm. The docking mechanism, which may also mechanically dock the manipulator arm to the carriage, provides an electrical interface between the carriage and the manipulator arm when the manipulator arm is docked thereto. The electrical power may be supplied by the manipulator arm to the carriage via this electrical interface when the manipulator arm is docked.

Electrical power may thus be supplied to the carriage when the manipulator arm is docked to the carriage. When the manipulator arm is undocked, no electrical connection is established between the manipulator arm and the carriage, and thus no electrical power can be supplied from the manipulator arm to the carriage.

This may have the advantageous effect that the carriage may not be actuated or otherwise electrically activated unless the manipulator arm is docked to the carriage. It is thus prevented that the carriage is inadvertently actuated in case the manipulator arm is not docked, which may disrupt the surgery and in extreme cases even endanger the patient or operating room staff. Effectively, if the manipulator arm is removed, the carriage is automatically deactivated by being disconnected from the electrical power supply. When the manipulator arm is docked, which typically involves the operator's attention also being focused on controlling the surgical robotic system, the carriage may be actuated. This provides a safe way of operating the robotic system.

In an equivalent embodiment, the electric actuator may be included in the suspension structure and supplied with electrical power via the carriage, e.g., via an electric interface between the carriage and the suspension structure, with the carriage itself being supplied with electrical power by the manipulator arm in the above described manner. This embodiment provides the same advantageous effects.

Optionally, the manipulator arm includes a first control circuit configured to control supply of the electrical power to one or more actuators in the manipulator arm, wherein the first control circuit is configured to prevent the supply of the electrical power to the one or more actuators if the manipulator arm is not docked to the carriage. Whereas the carriage may be automatically deactivated upon undocking of the manipulator arm, namely by being disconnected from the power supply, the manipulator arm may in some cases remain connected to the power supply even when undocked. In such a situation, actuation of electrical actuators in the manipulator arm may be unsafe or may at least not be desired since the manipulator arm may be in an unknown or undefined position. It may thus be desirable not only to deactivate the carriage upon undocking, but also to deactivate any actuators in the manipulator arm, and conversely, activate the carriage and the manipulator arm when the manipulator arm is docked. For that purpose, a control circuit may be provided, which in some embodiments is constituted by or included in a 'base' printed circuit board, to (de-)activate any electrical actuators when the manipulator arm is (un-)docked.

Optionally, the carriage includes a second control circuit configured to communicate with the first control circuit via the electrical connection when the manipulator arm is docked to the carriage, wherein the first control circuit is configured to prevent the supply of the electrical power to the one or more actuators if the first control circuit is unable to communicate with the second control circuit. Accordingly, the electric actuators in the manipulator arm may be activated when the control circuit in the manipulator arm is able to communicate with a corresponding control circuit in the carriage, which may thereby indicate that the manipulator arm is safely docked.

Optionally, the connector is configured to receive control data via the cable, wherein the control data includes carriage control data for controlling the movement of the carriage along the rail, wherein the manipulator arm is configured to provide the carriage with the carriage control data via the electrical connection. The above described connecting and disconnecting of the power supply thus also applies to any carriage control data which is provided via the cable to the manipulator arm.

Optionally, the manipulator arm includes a locking handle operable in an open and closed position, wherein the locking handle, when manually actuated from the open to the closed position, mechanically preloads and locks the docking mechanism. For example, the locking handle may in the closed position press both connectors of the docking mechanism together, e.g., using a mechanical force, to ensure sufficient electrical and/or mechanical contact between both connectors.

Optionally, the manipulator arm includes a handgrip for enabling the manipulator arm to be held before and/or after being docked to the carriage, wherein the locking handle physically blocks at least part of the handgrip in the closed position. The handgrip may be provided for enabling a user to hold the manipulator arm during docking and undocking. With the locking handle physically blocking at least part of the handgrip in the closed position, it may be immediately apparent for the user that he/she needs to first unlock the locking handle before attempting to undock the manipulator arm. Optionally, the locking handle may in the closed position physically block the handgrip to the extent that the user may not even be able to hold the handgrip.

Optionally, the locking handle in the open position physically blocks the connector, thereby blocking the cable from being connected to the connector. The locking handle may in the open position occupy a same space, e.g., above the connector, which would be occupied by the cable when connected to the connector. As such, if the cable is connected, the locking handle may not be put in the open position, or conversely, the cable may need to be disconnected for the locking handle to be put in the open position. This creates an additional safety mechanism as the user may first need to disconnect the cable before being able to undock the manipulator arm. Any unwanted actuation of the manipulator arm, or possible short circuit or electric shock to the user in case of a malfunction, may thus be prevented when the manipulator arm is undocked.

Optionally, the docking mechanism further includes mechanical alignment aids arranged on a first surface of the manipulator arm and complementary mechanical alignment aids arranged on a second surface of the carriage to provide mechanical alignment between the manipulator arm and the carriage during docking. By providing mechanical alignment aids, it may be ensured that the manipulator arm is docked to the carriage in a well-defined manner, e.g., at a known and constant position relative to each other.

Optionally, the mechanical alignment aids and the complementary mechanical alignment aids mutually interlock to establish a mechanical connection between the manipulator arm and the carriage when the manipulator arm is docked.

Optionally, the mechanical alignment aids include one or more cavities and the complementary mechanical alignment aids include one or more protrusions, such as semi-spheres, fitting the one or more cavities. Semi-spheres and similar type of protrusions may be advantageous since their rounded surfaces may prevent damage to drape(s) arranged in between the manipulator arm and the carriage.

Optionally, the second surface of the carriage is a top-facing surface, wherein the carriage further includes a bottom-facing surface, wherein the manipulator arm is arranged to clamp the carriage by exerting a clamping force to the top surface and the bottom surface when docked to the carriage. By the manipulator arm clamping the carriage from above and below, rather than, e.g., from the sides, the coupling is relatively robust for the user inaccurately positioning the manipulator arm with respect to the carriage during the docking procedure due to gravity force.

Optionally, during use of the surgical robotic system a drape is arranged in between the manipulator arm and the carriage, wherein the drape includes a drape interface for enabling the first docking connector to establish the electrical connection with the second docking connector through the drape. For example, the drape may include a hole which allows the connectors to mutually engage through the drape.

Optionally, the drape interface is an intermediate body including an electrical interface, wherein the first docking connector and the second docking connector are mutually positioned and/or shaped so that, when the manipulator arm is docked, the electrical connection is established if the drape is arranged with the intermediate body in between both connectors so as to establish the electrical interface between both connectors. Both connectors of the coupling mechanism may be designed such that, when the manipulator arm is docked to the carriage, an intermediate body may still be required in between both connectors to establish an electrical connection between the two connectors. This may ensure that the carriage and/or the manipulator arm is activated when a drape is correctly placed between the manipulator arm and the carriage, at least with respect to the drape's interface. For that purpose, the first connector and the second connector may be positioned and/or shaped such that without the intermediate body, an electrical connection cannot be established. This has the advantageous effect that an additional safety mechanism is provided which ensures that a drape is applied to the robotic system during use.

In a further aspect of the presently disclosed subject matter, a drape is provided including the drape interface. Such a drape may be separately manufactured and sold.

It will be appreciated by those skilled in the art that two or more of the above-mentioned embodiments, implementations, aspects and/or optional aspects of the presently disclosed subject matter may be combined in any way deemed useful.

BRIEF DESCRIPTION OF THE DRAWINGS

These and other aspects of the presently disclosed subject matter are apparent from and will be elucidated with reference to the embodiments described hereinafter. In the drawings.

Figure 1:
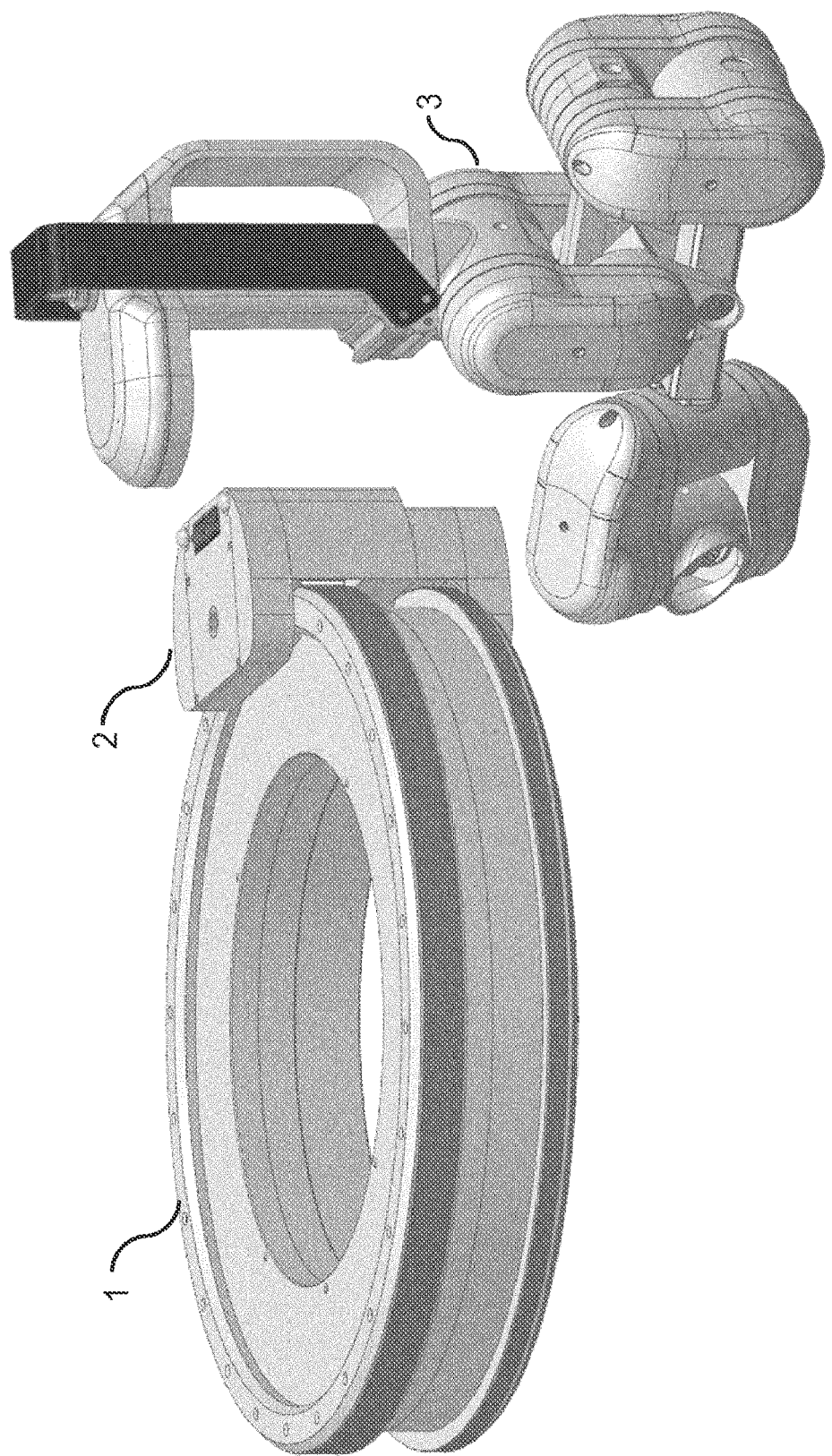
FIG. 1 shows part of a surgical robotic system, namely a suspension structure on which a carriage is mounted and a dockable manipulator arm.

It should be noted that items which have the same reference numbers in different figures, have the same structural features and the same functions, or are the same signals. Where the function and/or structure of such an item has been explained, there is no necessity for repeated explanation thereof in the detailed description.

LIST OF REFERENCE AND ABBREVIATIONS

The following list of references and abbreviations is provided for facilitating the interpretation of the drawings and shall not be construed as limiting the claims.

1 suspension structure
2 carriage
3 manipulator arm
4 guiding rails
5 driving rail
6 sensor ring
7 passive track rollers
8 active track roller
9 transmission
10 electric motor
11 motor encoder
12 ring encoder
13 carriage printed circuit board
14 docking connector
15 top portion of manipulator arm
16 base printed circuit board
17 data/power connector
18 data/power cable
19 docking printed circuit board
20 docking connector
21 set of semi-spheres
22 set of cavities
23 lock handle
24 handgrip
25 first drape
26 first drape interface
27 second drape
28 second drape interface

DETAILED DESCRIPTION OF EMBODIMENTS

FIG. 1 shows part of a surgical robotic system in the form of a suspension structure 1 on which a carriage 2 is mounted and a manipulator arm 3 which is dockable to the carriage 2. Together, the carriage 2 and the manipulator arm 3 form a manipulator unit. The manipulator unit may, in case the surgical robotic system is a master-slave robotic system, be a slave unit of the master-slave robotic system. It is noted that in addition to the parts described in this specification, the surgical robotic system may optionally further include conventional parts, including but not limited to one or more master units, an external control cabinet, an external power supply, etc.

Instead of mounting the manipulator arm 3 directly onto the suspension structure 1, the system shown in FIG. 1 includes three parts, namely the suspension frame 1, the carriage 2 which may be permanently or semi-permanently mounted to the suspension frame 1, and a manipulator arm 3 which may be attached, e.g., by docking, or removed from the carriage 2 in a manner as described further onwards.

In general, this partitioning may facilitate proper alignment of the carriage 2 with respect to the suspension structure 3, and may facilitate the unimpeded and uncompromised movement of the carriage 2 around the suspension structure 1. The movement may be actuated by the carriage 2 itself, e.g., by an electric actuator or electric motor in the carriage 2. In this case, the interface between the carriage 2 and the manipulator arm 3 may not need to transfer mechanical power. This may enable use of a relatively simple drape in between the carriage 2 and the manipulator arm 3. Namely, the drape does not have to be highly resilient to dynamic torques or forces that may otherwise damage the drape during movement. As a result, the interface between the carriage 2 and the manipulator arm 3 may be kept relatively simple.

Figure 2:
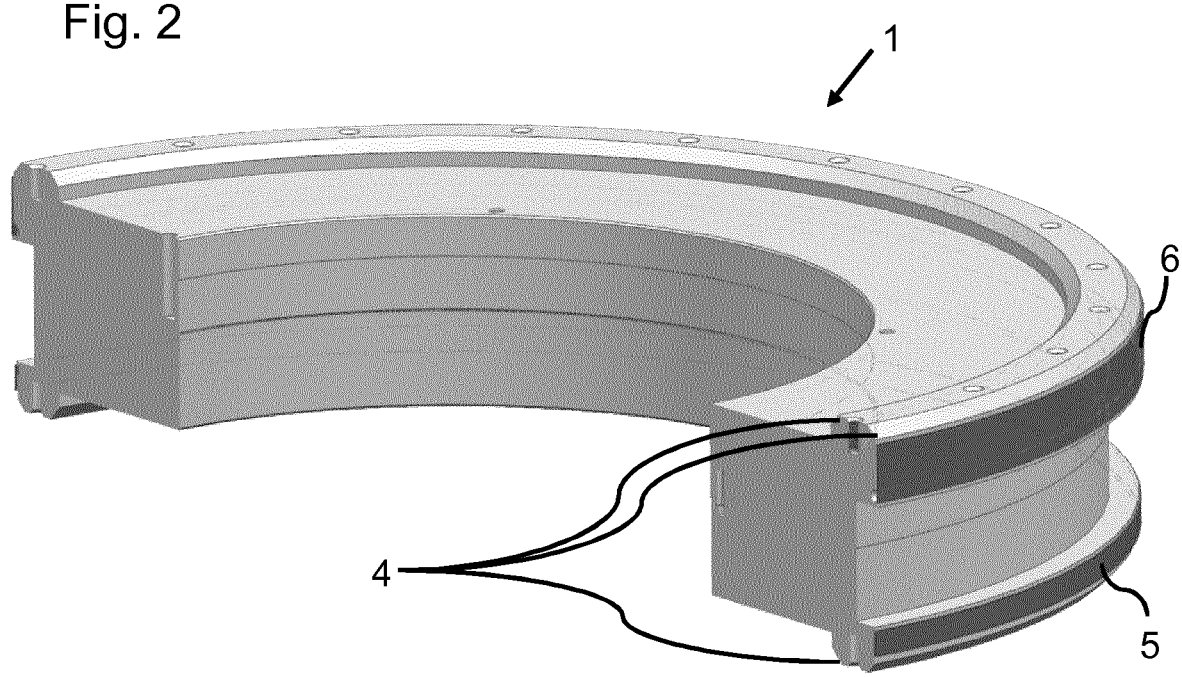
FIG. 2 provides a cross-sectional view of the suspension structure.

FIG. 2 provides a cross-sectional view of the suspension structure 1, which shown to include a set of guiding rails 4 and a driving rail 5, as well as a sensor ring 6 with a grating. It is noted that the suspension structure is by way of example a ring-shaped structure. Alternatively, the suspension structure may have any other shape, including but not limited to a partial ring-shaped structure, an elliptical structure, a curve, a straight line, etc., or may be constituted by a combination of such shapes.

Figure 3:
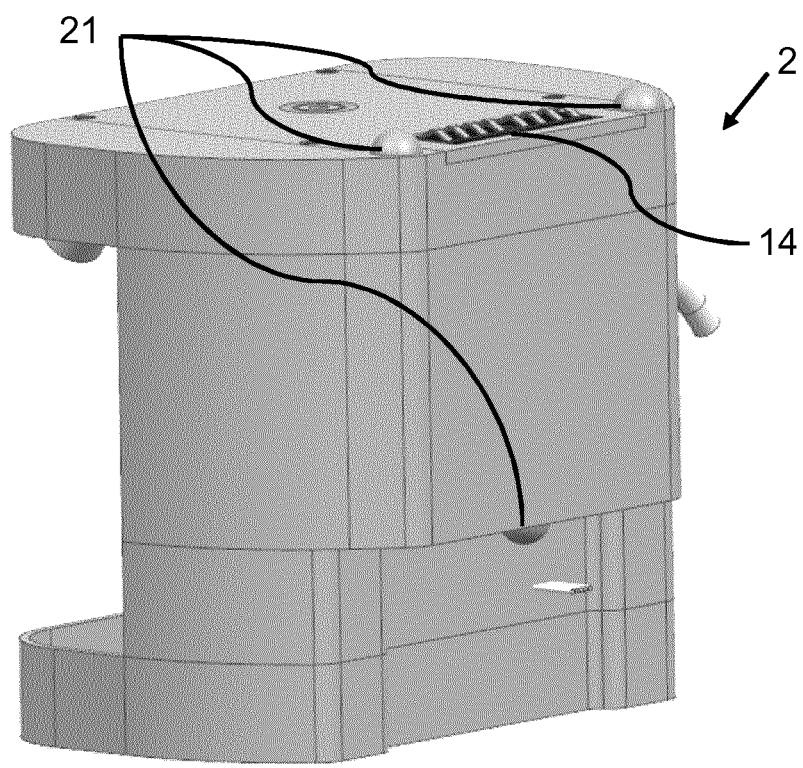
FIG. 3 shows the exterior of the carriage.

FIG. 3 provides a more detailed view of the exterior of the carriage 2 which is shown to include a male docking connector 14 and a set of semi-spheres 21.

Figure 4:
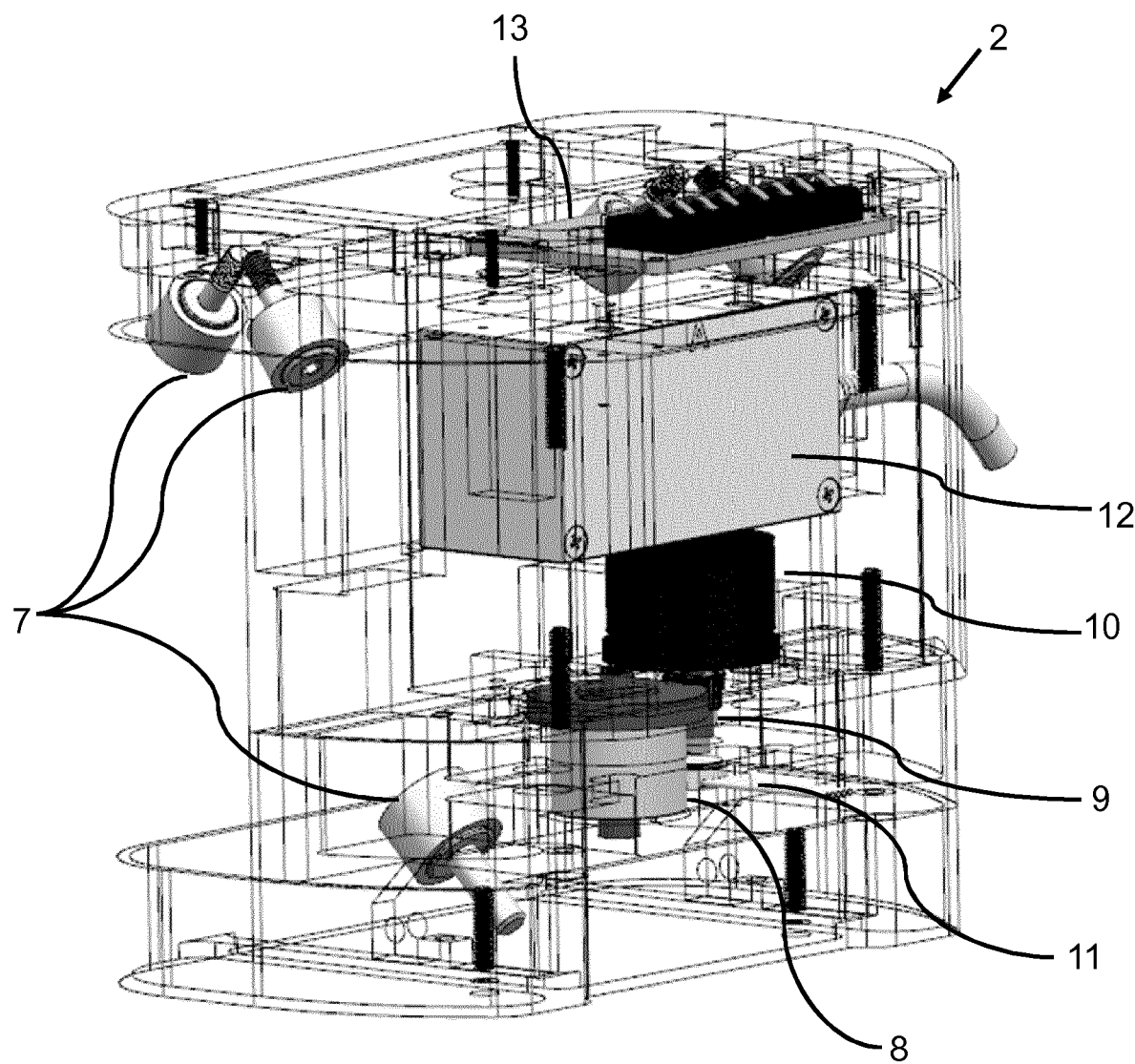
FIG. 4 provides a partially transparent view of the carriage.

FIG. 4 provides a partially transparent view of the carriage 2 which shows the carriage 2 including passive track rollers 7 which make contact with the guiding rails of the suspension structure and an active track roller 8 which makes contact with the driving rail of the suspension structure. The active track roller 8 may be actuated by a transmission 9 and an electric motor 10. The rotation of the motor shaft may be measured by a motor encoder 11. The carriage 2 may also include a ring encoder 12 which may measure the position of the carriage 2 along the sensor ring 6 of the suspension structure. The electric motor 10, the motor encoder 11 and the ring encoder 12 may be electronically connected to a carriage printed circuit board (PCB) 13 which may activate and control these components and which may communicate with other system components. The top part of the carriage PCB 13 may protrude from the top surface of the carriage 2 and include the male docking connector 14.

It will be appreciated that the carriage and the suspension structure may also have various other designs with respect to the movement of the carriage along and the attachment of the carriage to the suspension structure. For example, instead of using track rollers, the carriage may be guided along the suspension structure using one or more air bearings, planar bearings, linear bearings, spherical bearings, magnetic bearings, rods or plates, or an elastic mechanism. Similarly, instead of using an electric motor, or specifically a roller drive system, also a gear drive system, belt drive system, magnetic drive system, piezo actuator system or direct drive system may be used for effecting the movement of the carriage. In general any other suitable type of movably mounting a carriage to a suspension structure may be used.

Figure 5:
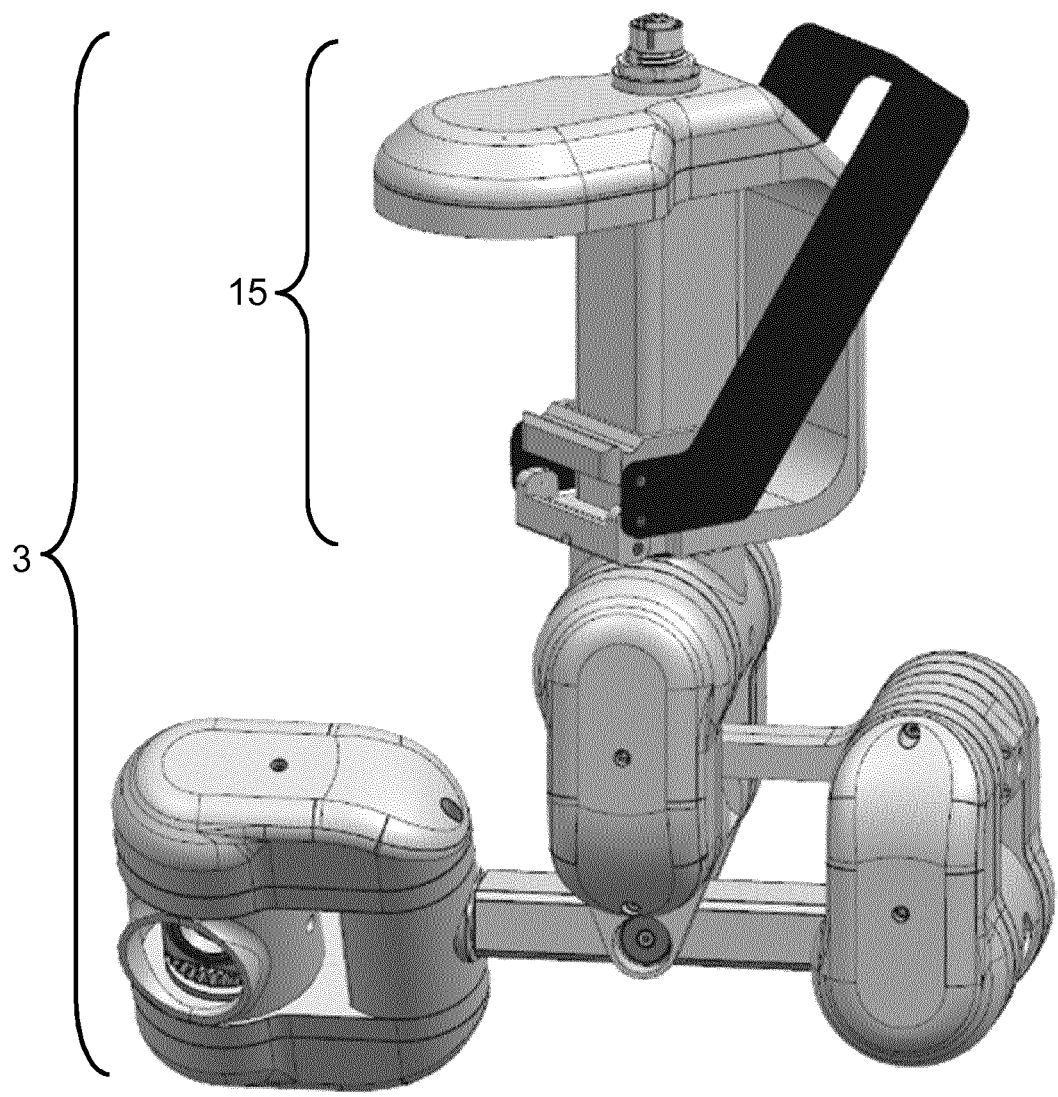
FIG. 5 shows the manipulator arm.
Figure 6:
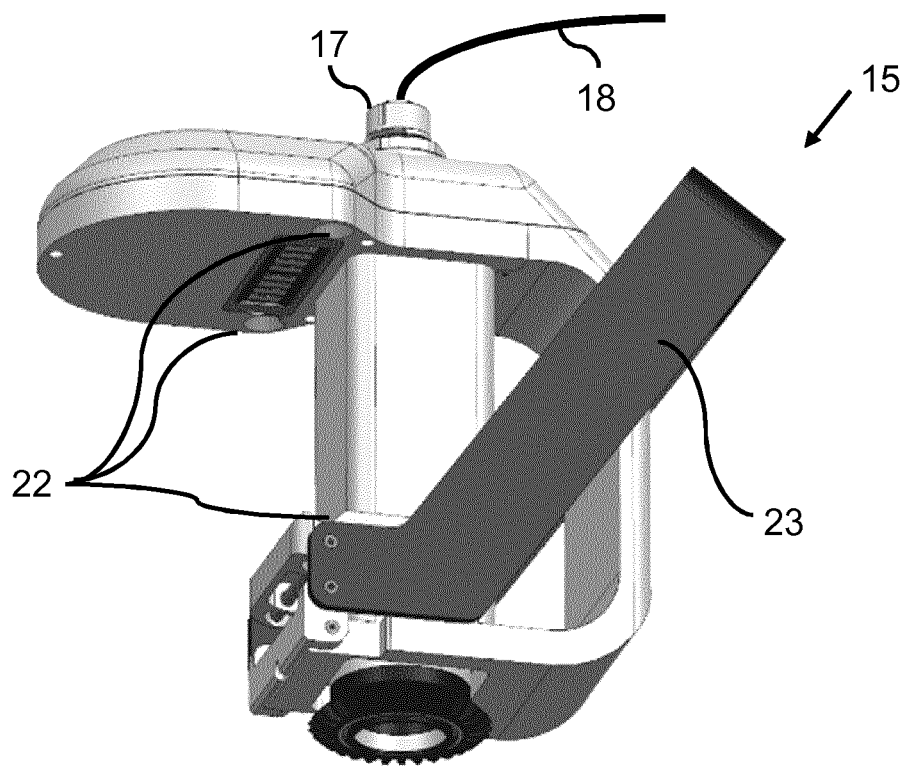
FIG. 6 shows the exterior of a top-portion of the manipulator arm.
Figure 7:
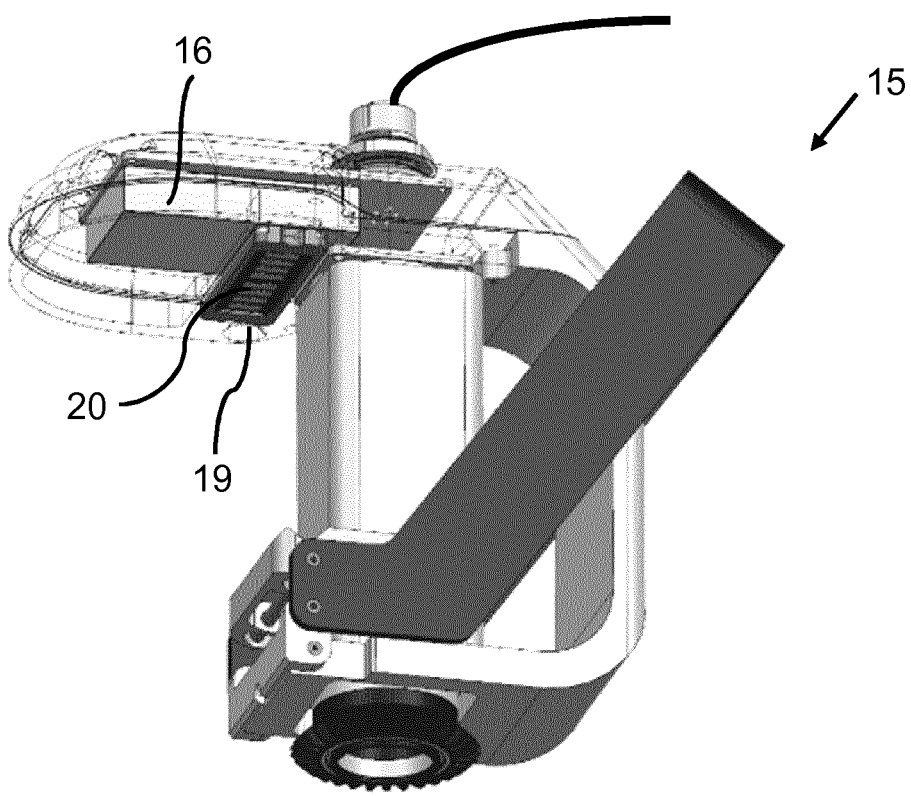
FIG. 7 provides a partially transparent view of the top-portion.

FIG. 5 shows the manipulator arm 3 including a top portion 15 of the manipulator arm, while FIG. 6 shows the exterior of the top-portion 15 and FIG. 7 provides a partially transparent view of the top-portion 15. As may also be seen in these figures, the top portion 15 may include a base PCB 16 that receives data and electrical power from a data/power cable 18 which may be connected to a data/power connector 17 of the manipulator arm 3. The data/power cable 18 may, during use, be connected to an external control cabinet (not shown) which may include an electric power supply, such as a connection to an electric main. The base PCB 16 may include a processing unit, communication IC, and other components for communicating with other system components and to activate and control the manipulator arm. The top portion 15 may also include a docking PCB 19 with a female docking connector 20 which may protrude from the bottom surface of the top portion 15, and which may be the counterpart of the male docking connector of the carriage. Alternatively, the docking PCB 19 and the base PCB 16 may be one element.

With further reference to FIG. 3, the top and bottom surface of the carriage 2 may include a number of semi-spheres 21 that serve as a reference for mechanical alignment/coupling with the top portion 15 of the manipulator arm 3. For that purpose, top portion 15 may include a set of cavities 22 that match with the semi-spheres 21. The top portion 15 may thus be mechanically aligned and coupled with carriage 2, whereas the docking connectors 14, 20 may be simultaneously aligned and coupled, creating an electromechanical docking between top portion 15 and the carriage 2.

It will be appreciated that also other types of mechanical alignment aids may be used instead of semi-spheres and corresponding cavities. For example, any protruding shape with a suitably rounded surface may be used together with corresponding cavities. It is further noted that the carriage may also include the cavities and the manipulator arm the protrusions, instead of the other way around.

It may be seen from the figures that the manipulator arm 3 and the carriage 2 may be designed such that when manipulator arm 3 is not docked to the carriage 2, e.g., by way of its top portion 15, electrical power is not transmitted from the base PCB 16 to the carriage 2 nor to electrical actuators of the manipulator arm 3 itself.

Figure 8:
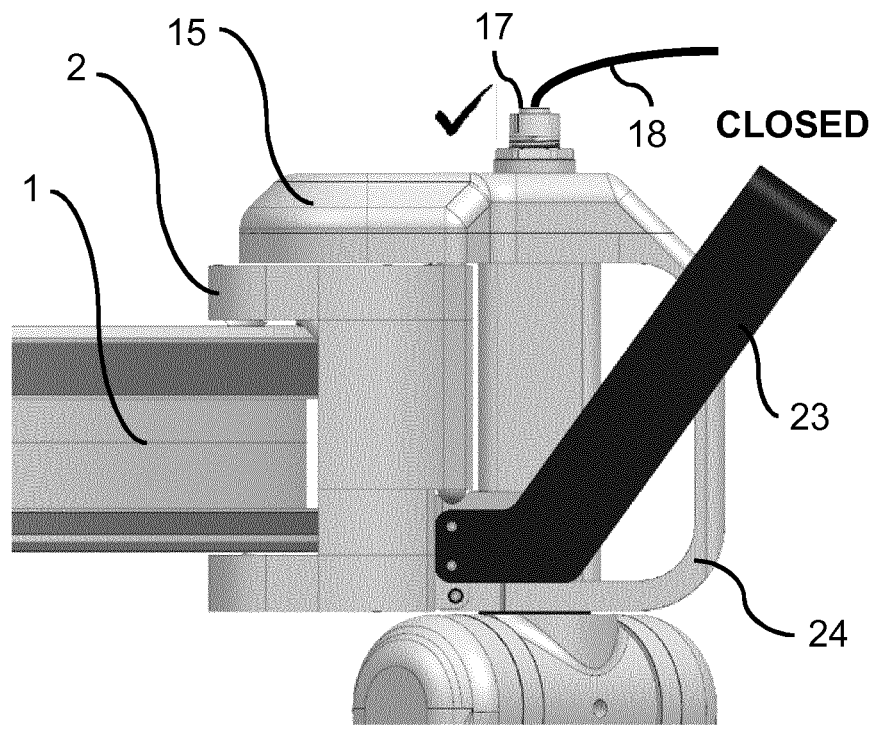
FIG. 8 shows the top-portion of the manipulator arm including a data/power connector and a locking handle which is positioned in a closed position.

FIG. 8 shows the top-portion 15 including a data/power connector 17 and a locking handle 23 which is positioned in a closed position. The locking handle 23 may operate a mechanism that preloads and locks the top portion 15 onto the carriage 2. As such, the closed position of the lock handle 23 may preload and lock the docking mechanism. In the closed position, the lock handle 23 may visually and mechanically block a handgrip 24, which may prevent the user from undocking the top portion 15 from the carriage 2 unless the lock handle is first placed into the open position.

Figure 9:
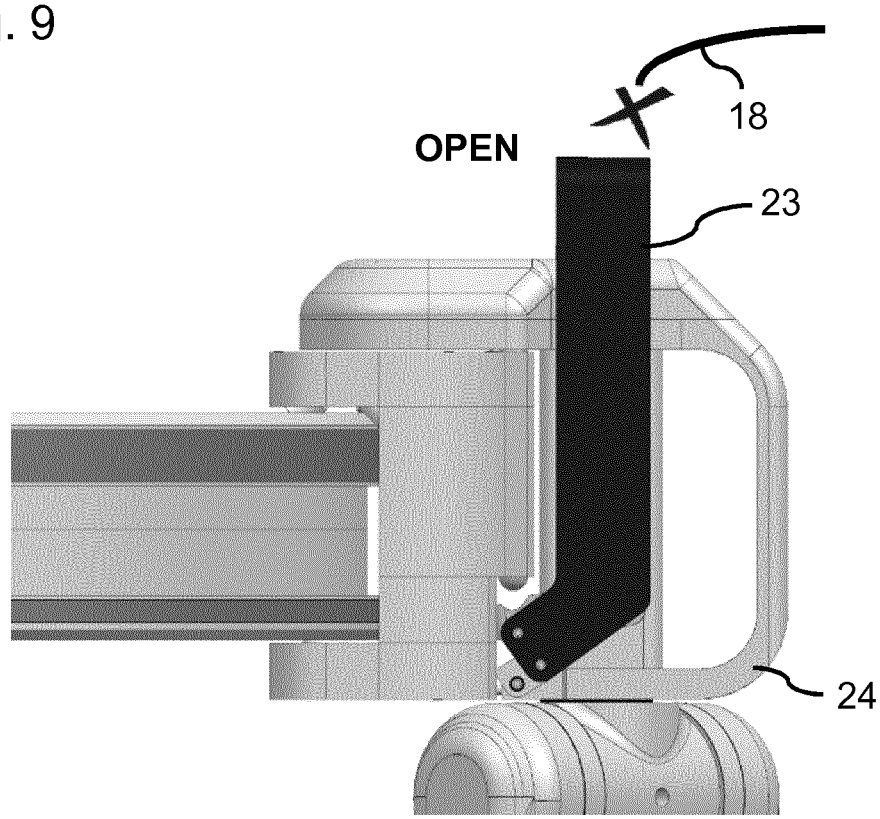
FIG. 9 is similar to FIG. 8 but shows the locking handle in an open position.

FIG. 9 shows the locking handle 23 in the open position, in which position the lock handle 23 may unlock the docking mechanism so that the top portion 15 may be attached to or removed from the carriage 2. As can be seen in FIG. 9, the open position of the lock handle 23 may be reached if the data/power cable 18 is not connected. Accordingly, the top portion 15 may be attached to or removed from the carriage 2 if the data/power cable 18 is not connected to the connector 17.

It will be appreciated that the combination of previously described measures may create a triple safety mechanism for the manipulator unit to become active. Namely, 1) the manipulator arm and carriage may need to be docked, 2) the lock handle may need to be in a closed position, and 3) the data/power cable may need to be connected. If any of these requirements is not met, the manipulator arm and the carriage may, by way of the measures, both be inactive. If all or most of these requirements are met, the manipulator arm and carriage may become active. Moreover, the manipulator arm cannot be active while the carriage is inactive, and vice versa. By design, the user may automatically be guided towards following the correct procedure to dock or undock the manipulator arm in a safe way. This triple safety mechanism may prevent use errors that may lead to a hazardous situation in which the elements of the docking mechanism are not properly connected but still activated, leading to potentially dangerous or unstable movement. The triple safety mechanism may also ensure that in case of technical failure within the manipulator unit, the manipulator unit as a whole becomes inactive but remains in a passively safe state.

It will be appreciated that, although advantageous, it is not needed for all or most measures of the triple safety mechanism to be implemented together. Rather, individual measures may already obtain improvements over known robotic systems.

Figure 10:
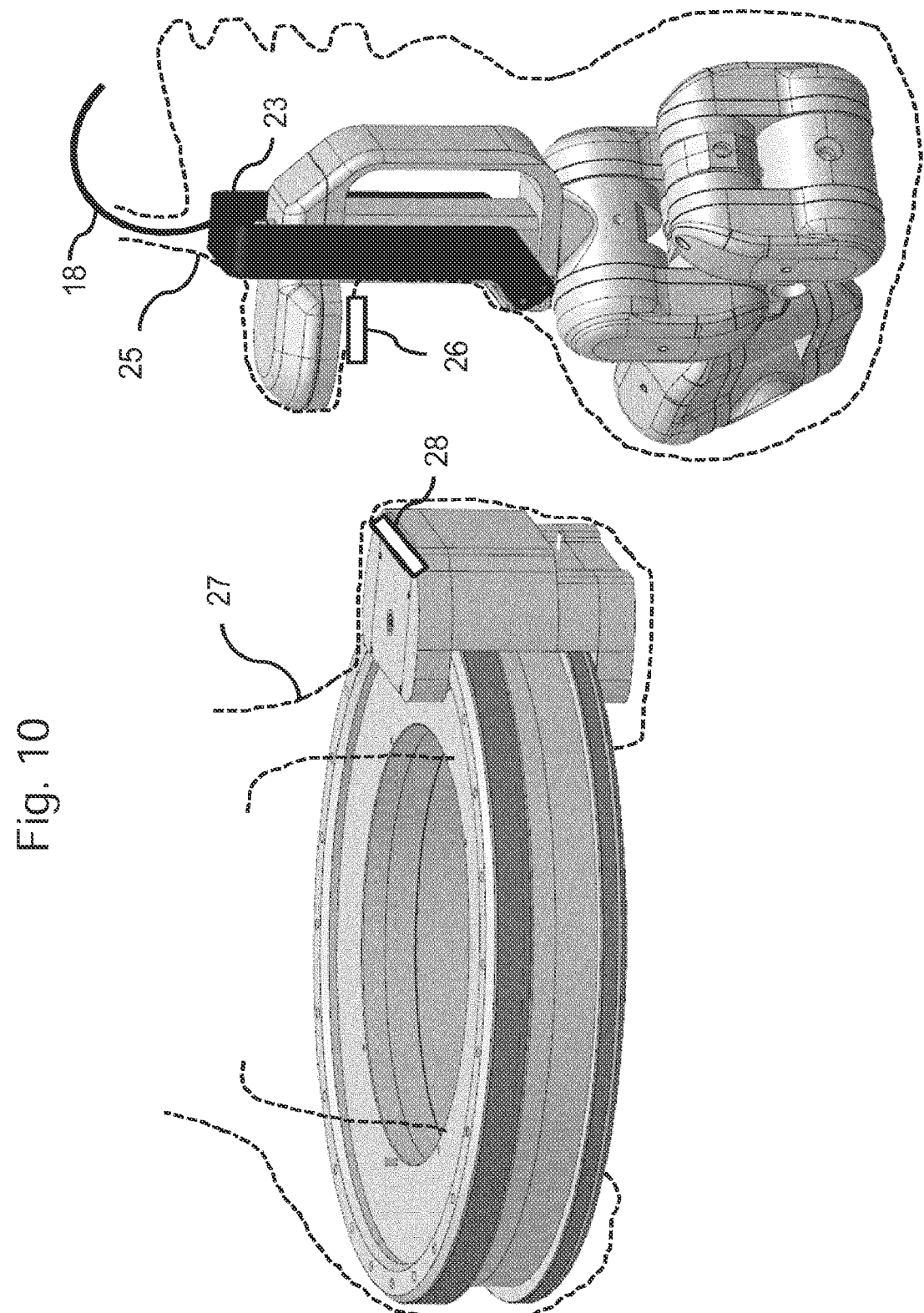
FIG. 10 illustrates the draping of the surgical robotic system.

FIG. 10 illustrates the draping of the robotic system, which may include two separate parts. A first drape 25 may envelope the manipulator arm 3. As previously described, the bottom surface of the top portion of the manipulator arm 3, including the alignment cavities, may be designed to be sufficiently smooth to avoid rupture of the sterile draping 25 caused by sharp edges. The first drape 25 may include a drape interface 26 that allows transmission of electrical power and data to and from the female docking connector of the manipulator top portion. The drape interface 26 may be a hole and seal, or an intermediate body, or an intermediate body with a bridging connector, or a bridging connector enclosed in the draping. The first drape 25 may be designed to have sufficient slack to enable proper usability of the lock handle 23.

A second drape 27 may envelop the suspension structure 1 and the carriage 2. As previously described, the outer surface of the carriage 2, including the semi-spherical alignment protrusions 21, may be designed to be sufficiently smooth to avoid rupture of the sterile draping 27 caused by sharp edges. The second drape 27 may include a drape interface 28 that allows transmission of electrical power and data to and from the male docking connector of the carriage 2. The drape interface 28 may be a hole and seal, or an intermediate body, or an intermediate body with a bridging connector, or a bridging connector enclosed in the draping.

Figure 11:
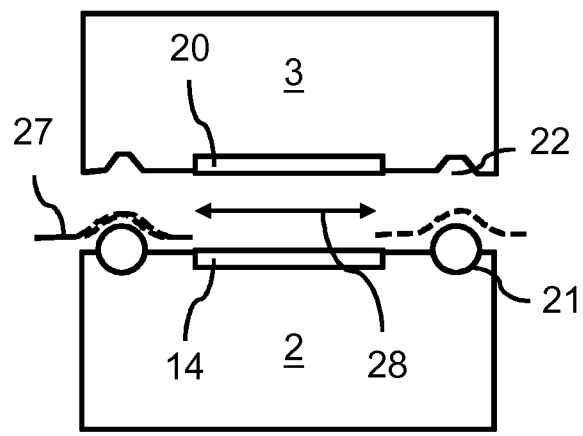
FIGS. 11 and 12 each provide a cross-sectional view of the docking mechanism when a drape is applied having a hole as drape interface.
Figure 12:
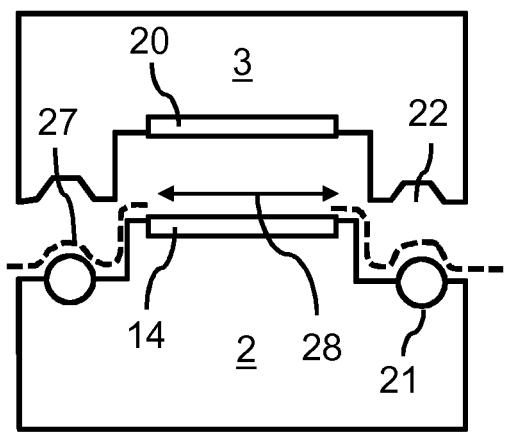

FIGS. 11 and 12 show cross-sections of different docking interfaces between the carriage 2 and the manipulator arm 3, with FIG. 11 showing a flat contact surface and FIG. 12 showing a recessed/protruding contact surface. In both figures, the mechanical alignment aids 21, 22, the connectors 14, 20 and a drape 27 are shown, with the drape being in this example the second drape 27 but also applying to the first drape. Here, the drape interface 28 includes a hole and (not explicitly shown) a seal around the hole. The connectors 14, 20 may mutually engage through the hole if the manipulator arm 3 is docked and thus brought into contact with the carriage 2.

Figure 13:
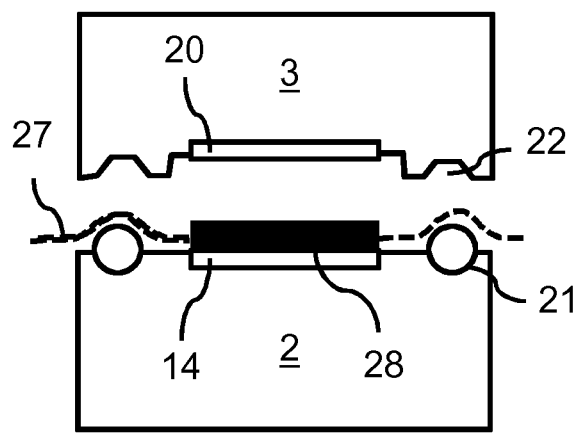
FIGS. 13 and 14 each provide a cross-sectional view of the docking mechanism when a drape is applied having an intermediate body as drape interface.
Figure 14:
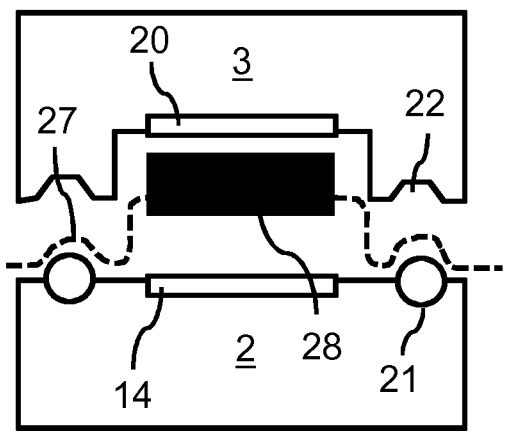

FIGS. 13 and 14 show cross-sections of different docking interfaces between the carriage 2 and the manipulator arm 3 where the connectors 14, 20 are mutually positioned so that, when the manipulator arm 3 is docked, the electrical connection is established if the drape 27 is arranged in between both connectors so as to establish the electrical interface between both connectors. For that purpose, the drape interface 28 may be constituted or include an intermediate body 28 which functions as an electrical interface between the two connectors 14, 20. In these examples, when the manipulator arm 3 is docked to the carriage 2, the intermediate body may mechanically and/or electrically bridge the gap between both connectors.

Although shown in FIGS. 13 and 14 for one drape 27, the docking connectors 14, 20 and the drape interfaces of both drapes may be designed such that both drapes need to be applied so as to mechanically and/or electrically bridge the gap between both connectors. For example, one drape interface alone may be insufficient to mechanically and/or electrically bridge the gap between both connectors, e.g., by being insufficiently thick or not establishing a complete electrical interface.

In general, the drape interface(s) may provide a fourth safety mechanism, in that an electrical power and/or data connection between the carriage 2 and the manipulator arm 3 may be created if at least one of the drape interfaces 25, 26, or in an embodiment both of the drape interfaces 25, 26, are properly aligned and thus if drapes 25, 27 are applied. As a result, the fourth safety mechanism may ensure that a sterile barrier is in place before the system becomes active. Conversely, if the drape(s) are not there, the components of the robotic system remain inactive.

It will be appreciated that the docking mechanism which is described within the context of a manipulator unit, such as a slave unit of a master-slave robot, may also be applied in a master unit of a master-slave robot. The master unit may be movably attached to a suspension structure in a manner as described for the manipulator unit. Rather than including a manipulator arm, the master unit may include an input device, such as but not limited to a joystick or any other (combination of) input modality. The input device may be dockable to a carriage in the same manner as described for the manipulator arm. The same advantageous effects may be obtained.

Modifications of the master unit which correspond to the described modifications of the manipulator unit are within reach of the skilled persons.

It should be noted that the above-mentioned embodiments illustrate rather than limit the presently disclosed subject matter, and that those skilled in the art will be able to design many alternative embodiments.

In the claims, any reference signs placed between parentheses shall not be construed as limiting the claim. Use of the verb "includes" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage.

The invention claimed is:

1. A surgical robotic system, comprising:
a suspension structure including a rail; and
a manipulator unit including
a carriage arranged to be mounted to the suspension structure, wherein the carriage includes an electric actuator for movement of the carriage along the rail, and
a manipulator arm arranged to be detachably docked to the carriage via a docking mechanism, wherein
the docking mechanism includes a first docking connector on the manipulator arm and a second docking connector on the carriage, and the first and the second docking connector establish an electrical connection between the manipulator arm and the carriage when the manipulator arm is docked,
wherein the manipulator arm includes a connector for connecting the manipulator arm via a cable to an electric power supply, and
wherein the manipulator arm is configured to supply the carriage with the electrical power via the electrical connection when the manipulator arm is docked.

2. The surgical robotic system according to claim 1, wherein the manipulator arm includes a first control circuit configured to control supply of the electrical power to one or more actuators in the manipulator arm, wherein the first control circuit is configured to prevent the supply of the electrical power to the one or more actuators if the manipulator arm is not docked to the carriage.

3. The surgical robotic system according to claim 2, wherein the carriage includes a second control circuit configured to communicate with the first control circuit via the electrical connection when the manipulator arm is docked to the carriage, wherein the first control circuit is configured to prevent the supply of the electrical power to the one or more actuators if the first control circuit is unable to communicate with the second control circuit.

4. The surgical robotic system according to claim 3, wherein the connector is configured to receive control data via the cable, wherein the control data includes carriage control data for controlling the movement of the carriage along the rail, wherein the manipulator arm is configured to provide the carriage with the carriage control data via the electrical connection.

5. The surgical robotic system according to claim 3, wherein the manipulator arm includes a locking handle operable in an open and closed position, wherein the locking handle, when manually actuated from the open to the closed position, mechanically preloads and locks the docking mechanism.

6. The surgical robotic system according to claim 2, wherein the connector is configured to receive control data via the cable, wherein the control data includes carriage control data for controlling the movement of the carriage along the rail, wherein the manipulator arm is configured to provide the carriage with the carriage control data via the electrical connection.

7. The surgical robotic system according to claim 2, wherein the manipulator arm includes a locking handle operable in an open and closed position, wherein the locking handle, when manually actuated from the open to the closed position, mechanically preloads and locks the docking mechanism.

8. The surgical robotic system according to claim 1, wherein the connector is configured to receive control data via the cable, wherein the control data includes carriage control data for controlling the movement of the carriage along the rail, wherein the manipulator arm is configured to provide the carriage with the carriage control data via the electrical connection.

9. The surgical robotic system according to claim 8, wherein the manipulator arm includes a locking handle operable in an open and closed position, wherein the locking handle, when manually actuated from the open to the closed position, mechanically preloads and locks the docking mechanism.

10. The surgical robotic system according to claim 1, wherein the manipulator arm includes a locking handle operable in an open and closed position, wherein the locking handle, when manually actuated from the open to the closed position, mechanically preloads and locks the docking mechanism.

11. The surgical robotic system according to claim 10, wherein the manipulator arm includes a handgrip for enabling the manipulator arm to be held before and/or after being docked to the carriage, wherein the locking handle physically blocks at least part of the handgrip in the closed position.

12. The surgical robotic system according to claim 10, wherein the locking handle in the open position physically blocks the connector, thereby blocking the cable from being connected to the connector.

13. The surgical robotic system according to claim 1, wherein the docking mechanism further comprises mechanical alignment aids arranged on a first surface of the manipulator arm and complementary mechanical alignment aids arranged on a second surface of the carriage to provide mechanical alignment between the manipulator arm and the carriage during docking.

14. The surgical robotic system according to claim 13, wherein the mechanical alignment aids and the complementary mechanical alignment aids mutually interlock to establish a mechanical connection between the manipulator arm and the carriage when the manipulator arm is docked.

15. The surgical robotic system according to claim 13, wherein the mechanical alignment aids include one or more cavities and the complementary mechanical alignment aids include one or more protrusions fitting the one or more cavities.

16. The surgical robotic system according to claim 13, wherein the second surface of the carriage is a top-facing surface, the carriage includes a bottom-facing surface, and the manipulator arm is arranged to clamp the carriage by exerting a clamping force to the top surface and the bottom surface when docked to the carriage.

17. The surgical robotic system according to claim 1, wherein during use of the surgical robotic system, a drape is arranged in between the manipulator arm and the carriage, and the drape includes a drape interface for enabling the first docking connector to establish the electrical connection with the second docking connector through the drape.

18. The surgical robotic system according to claim 17, wherein the drape interface is an intermediate body including an electrical interface, and the first docking connector and the second docking connector are mutually positioned and/or shaped so that, when the manipulator arm is docked, the electrical connection is only established if the drape is arranged with the intermediate body in between both connectors so as to establish the electrical interface between both connectors.

19. The surgical robotic system according to claim 1, wherein the surgical robotic system is a master-slave robotic system, and the manipulator unit is a slave unit.

* * * * *